(12) United States Patent
Viscomi

(10) Patent No.: US 9,763,749 B2
(45) Date of Patent: Sep. 19, 2017

(54) COMPRESSIBLE COMPOSITE SHAPING INSTRUMENT

(71) Applicant: Ivoclar Vivadent AG, Schaan (LI)

(72) Inventor: Brian D. Viscomi, Easton, PA (US)

(*) Notice: Subject to any disclaimer, the term of this patent is extended or adjusted under 35 U.S.C. 154(b) by 709 days.

(21) Appl. No.: 14/138,377

(22) Filed: Dec. 23, 2013

(65) Prior Publication Data

US 2014/0199660 A1 Jul. 17, 2014

Related U.S. Application Data

(63) Continuation of application No. 12/154,872, filed on May 28, 2008, now Pat. No. 8,616,880.

(60) Provisional application No. 60/932,131, filed on May 29, 2007.

(51) Int. Cl.
| | | |
|---|---|---|
| A61C 3/08 | (2006.01) | |
| A61C 5/04 | (2006.01) | |
| A61C 5/50 | (2017.01) | |
| A61C 5/62 | (2017.01) | |

(52) U.S. Cl.
CPC ............... *A61C 5/04* (2013.01); *A61C 3/08* (2013.01); *A61C 5/50* (2017.02); *A61C 5/62* (2017.02)

(58) Field of Classification Search
CPC ........... A61C 5/04; A61C 5/062; A61C 5/064; A61C 5/125; A61C 5/50; A61C 3/108; A61K 6/02
See application file for complete search history.

(56) References Cited

U.S. PATENT DOCUMENTS

| | | | | |
|---|---|---|---|---|
| 3,628,249 A * | 12/1971 | Wurl | ...................... | A61C 5/125 |
| | | | | 433/162 |
| 5,129,825 A * | 7/1992 | Discko, Jr. | ............. | A61C 5/066 |
| | | | | 222/325 |
| 5,707,234 A * | 1/1998 | Bender | .................. | A61C 5/066 |
| | | | | 433/82 |
| 5,788,499 A * | 8/1998 | Hoffman | .................. | A61C 5/85 |
| | | | | 433/149 |
| 5,842,488 A * | 12/1998 | Belleau | .................. | A45D 34/04 |
| | | | | 132/320 |
| 6,503,084 B2 * | 1/2003 | Evers | ...................... | A61C 5/066 |
| | | | | 433/226 |
| 2003/0013066 A1* | 1/2003 | Dragan | .................. | A61C 5/062 |
| | | | | 433/90 |
| 2006/0251704 A1* | 11/2006 | Lin | .......................... | A61K 8/19 |
| | | | | 424/443 |
| 2007/0172789 A1* | 7/2007 | Muller | ................... | A61C 5/066 |
| | | | | 433/90 |
| 2007/0259313 A1* | 11/2007 | Dragan | ................ | A61C 9/0033 |
| | | | | 433/136 |
| 2009/0092563 A1* | 4/2009 | Allred | .................. | A61C 19/066 |
| | | | | 424/53 |

* cited by examiner

*Primary Examiner* — Yogesh Patel
(74) *Attorney, Agent, or Firm* — Hodgson Russ LLP

(57) ABSTRACT

A compressible dental instrument to non-impressively adapt restorative material through compression comprises a handle portion (2), having a docking aperture (4) to interface with a highly compressible foam insert (10) with a docking extrusion and a tip holder (14) having highly compressible tip (16). A user can dock both to compressively adapt composite resin to a tooth's surface by first applying a restorative to a tooth and second applying the compressible portion to the restorative. Applied pressure compresses the tip to non-impressively micro manipulate composite resin.

12 Claims, 25 Drawing Sheets

COMPRESSIBLE COMPOSITE SHAPING INSTRUMENT

CROSS REFERENCE TO RELATED APPLICATIONS

This application claims the benefit of Provisional Patent Application Ser. No. 60/932,131 filed 2007 May 29, by the present inventor

FEDERALLY SPONSORED RESEARCH

Not Applicable

SEQUENCE LISTING OR PROGRAM

Not Applicable

BACKGROUND FIELD OF INVENTION

This invention applies to the field of Dentistry, in particular, to provide for a disposable instrument specifically designed to manipulate a dental restorative material through compressive adaptation.

BACKGROUND PRIOR ART

The introduction of light-cured composite (resin filled) restorative materials to the dentist's armamentarium has presented him with filling materials which have distinct intrinsic properties quite different from the traditional amalgam (mercury based) restorative. In particular, composites present with a stickiness quality which undesirably adhere to traditional instrumentation during the restorative handling phases of the procedures. This adherence interferes with the release of the instrument upon withdrawing from the site of resin administration. Hence pull-back of the adhering resin makes it difficult to properly insert and adapt the resin to the prepared tooth. Furthermore, resin's displacement rather than compaction capabilities renders traditional instrumentation ineffective during the adaptive process. To address this inadequacy, there exists a myriad of composite specific instruments, for example, Teflon-based, and metal instruments with anti-stick coatings have been made available to the profession.

Both of these modalities in general are effective in minimizing the adherence factor of the resin, and do allow for the manipulation of the composite within the confines of the cavity preparation. However, because of the hardness of the instrument head, and the readily displaceable properties of the resin, application of the instrument head to the uncured resin mass typically results in a random movement of the resin mass and a residual imprint of the instrument head upon removal of the instrument. This can be problematical especially in areas of cosmetic concern. In particular, anterior (front) teeth, where resin thickness must be uniform and micro adapted to sensitive gum line margins, it is desirable and imperative to displace the resin in a uniform and predictable manner with instrumentation. The heretofore mentioned instruments do not permit micro manipulation of the resin, and furthermore can impart a residual indentation on the uncured resin such that further address of the instrument is necessary, or correction is due following resin polymerization. In that case, it is necessary to reshape the uneven cured resin, and the addition of more resin which can cause a repetition of the above cycle.

The compressible composite instrument by contrast: will not adhere to the resin, and because of its resilient properties allows the uncured resin to be micro-manipulated to tooth margins without imparting a tell-tale "footprint" through the emulsion cover onto the uncured resin. This can result in fewer addresses to the resin mass with subsequent economies of time realized and a more satisfactory end result.

Accordingly, several advantages of the present patent application compressible composite shaping instrument are:
1. An adherent resistant resin instrument.
2. Non-impressive micro-manipulation of composite resin dramatically reduces resin pullback upon withdrawal of the instrument.
3. Non-impressive manipulation of composite resin produces seamless ultra thin feathering.
4. Capable of micro-displacing of resin through a protective sheath or emulsion.
5. Compressible nature envelops resin leaving no discernable "footprint" in the uncured resin upon application and withdrawal of the instrument head.
6. Disposability obviates infection control considerations.

SUMMARY OF THE INVENTION

It is thus the object of this invention to provide for an instrument with a disposable highly compressible foam instrument portion to compressively adapt uncured composite resin. It is a further intention of this instrument to manipulate uncured resin which is sheathed within an emulsion layer to a tooth. Additionally this invention allows for minimally impressive micro-manipulation of uncured resin without resin pullback during instrument withdrawal. Lastly, the non-impressive nature of the instrument's foam head imparts a substantially minimal imprint or demarcation line upon application to the uncured resin's surface.

Figure 1A:
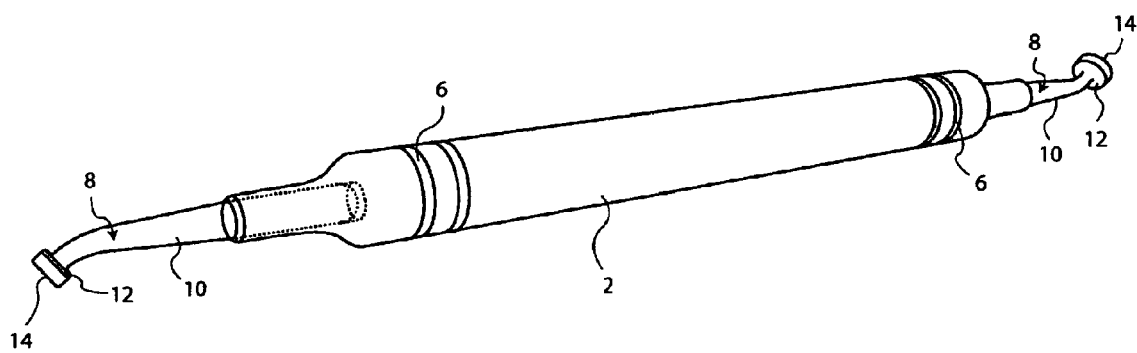
FIGS. 1A to 1B show various views of a preferred embodiment of the compressible composite shaping instrument having a gripping handle and compressible insert with an attached compressible applicator.

| DRAWINGS - REFERENCE NUMERALS |
| --- |
| 2. Handle |
| 4. Docking aperature |
| 6. Gripping grooves |
| 8. Compressible insert |
| 10. Insert body |
| 12. Tip Holder |
| 14. Compressible applicator |
| 16. Insert taper point |
| 18. Surface indentations |
| 20. Restorative material |
| 22. Compressible forces |
| 24. Expansive movement |
| 26. Non-impressed resin |
| 28. Tooth surface |
| 30. Gum-line compressible insert |
| 32. Inter-proximal compressible insert |
| 34. Wedge brush compressible insert |
| 36. Condensing compressible insert |
| 38. Operator |
| 40. Prepared anterior tooth surface |
| 42. Prepared posterior tooth |
| 44. Multi headed compressible insert |
| 46. Shaping blade |
| 48. Compressible tool |
| 50. Self adhesive applicator |
| 52. Peel away layer |
| 54. Adhesive surface |
| 56. Chisel compressible applicator |
| 58. Conical compressible applicator |
| 60. Internal tip stabilizer |
| 62. External tip stabilizer |
| 64. Multi-core compressible tip |
| 66. External layer |
| 68. Sheathed foam core |
| 70. Coated applicator |
| 72. Veneered applicator |
| 74. Flexible body |
| 76. Flexion core |
| 78. Sheathed shaping blade |
| 80. Multi tipped insert |
| 82. Snap in compressible applicator |
| 84. Compressible sheath |
| 86. Sheath liner |
| 88. Aperature compressible insert |
| 90. Insert docking aperature |
| 92. snapping ring |
| 94. Handle docking extrusion |
| 96. Friction groove |
| 98. Snapping groove |
| 100. Anti rotational groove |
| 102. Anti rotational extrusion |
| 104. Faceted insert body |
| 106. Threaded insert body |
| 108. Snap insert body |
| 110. Graspable compressible insert |
| 112. Preformed Veneer with applicator sheath |
| 114. Uncured restorative layer |
| 116. Applicator sheath |

DETAILED DESCRIPTION OF THE INVENTION

Figure 1B:
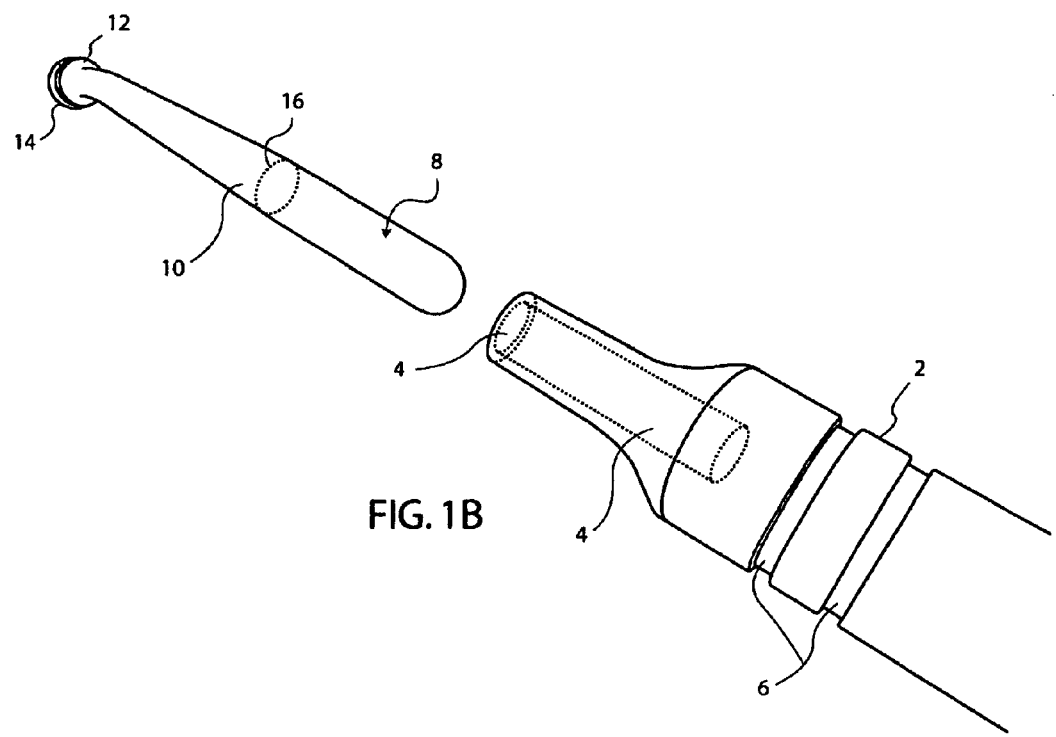
Figure 2:
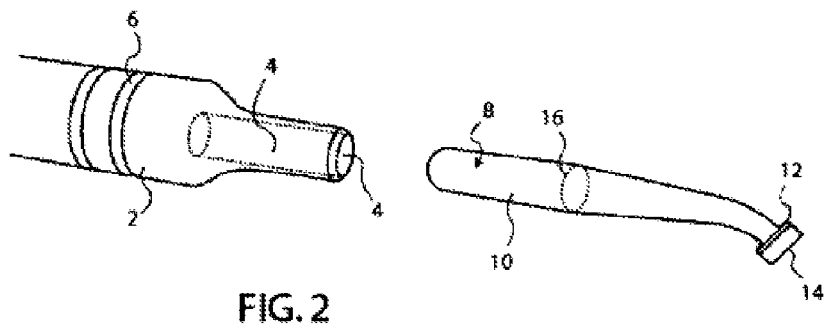
FIG. 2 shows details of a compressible insert's taper point before and after it's docking with a gripping handle's apertures.
Figure 3A:
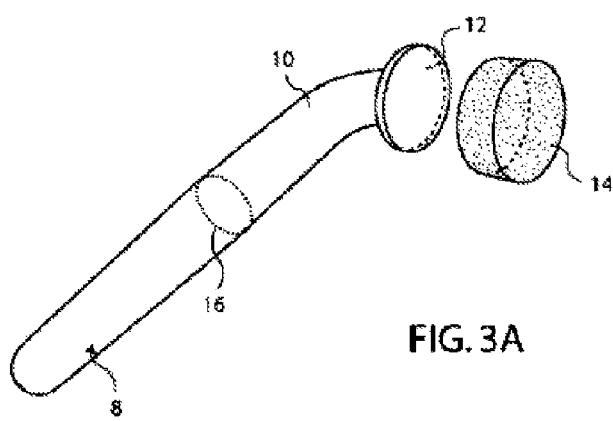
FIGS. 3A to 3B show a view of the compressible applicator and a close up view of the compressible applicator's surface indentations.
Figure 3B:
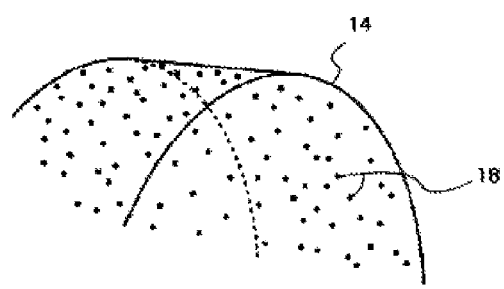

FIGS. 1A and 1B show dimensional views of the preferred embodiment's handle and compressible insert. FIG. 2 shows an insert's taper point relative to the handle's aperture when inserted. FIG. 3A shows compressible applicator attached and unattached from an insert's holder. FIG. 3B shows a close-up view of an applicator's indented surface.

Figure 4A:
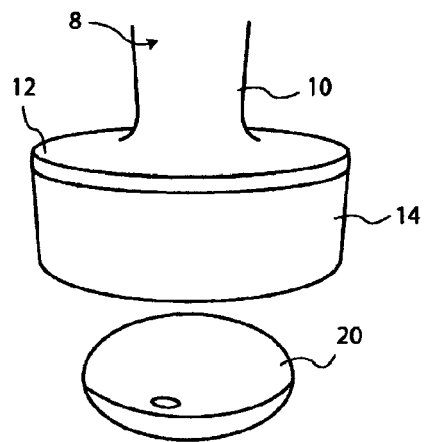
FIGS. 4A to 4C show a progressive sequence of composite resin being compressively expanded without making surface impressions.
Figure 4B:
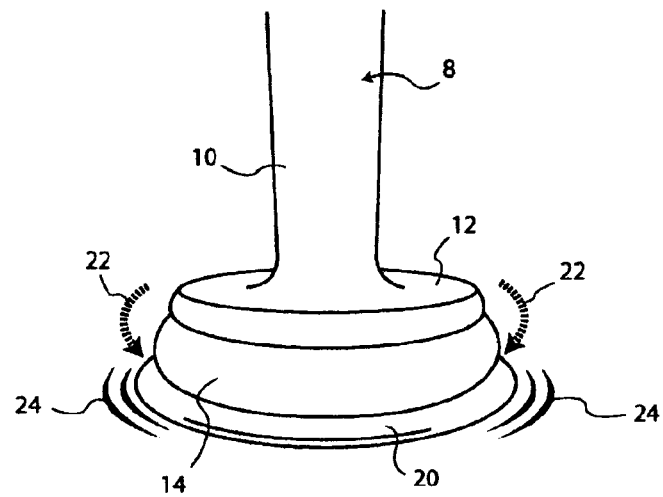
Figure 4C:
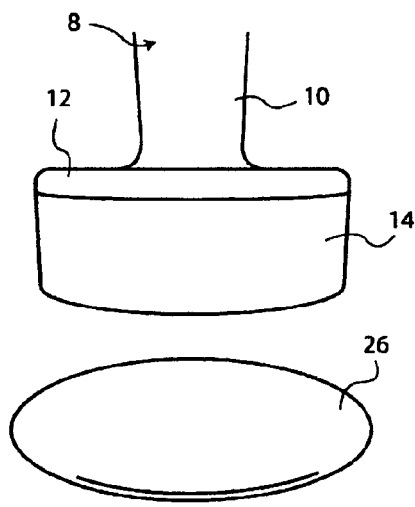
Figure 5:
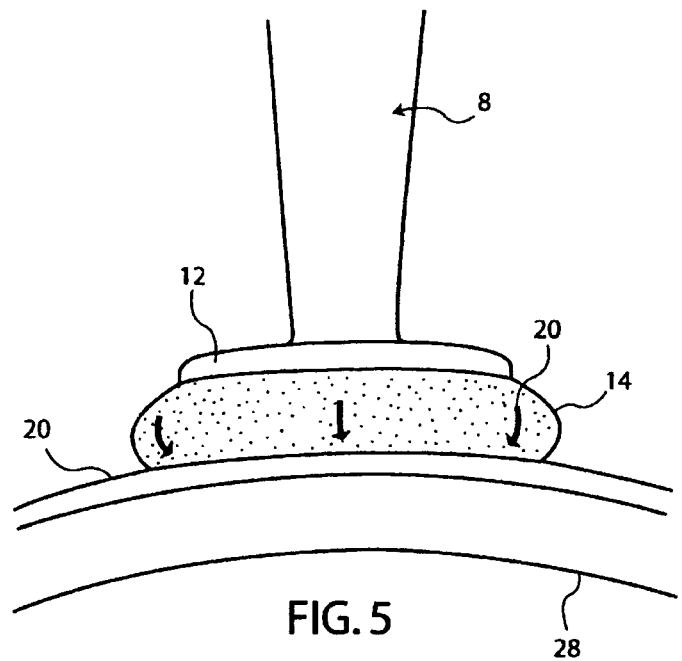
FIG. 5 shows an inferior view of a compressible applicator adaptively compressed against a restorative layer on a convex tooth surface.
Figure 6:
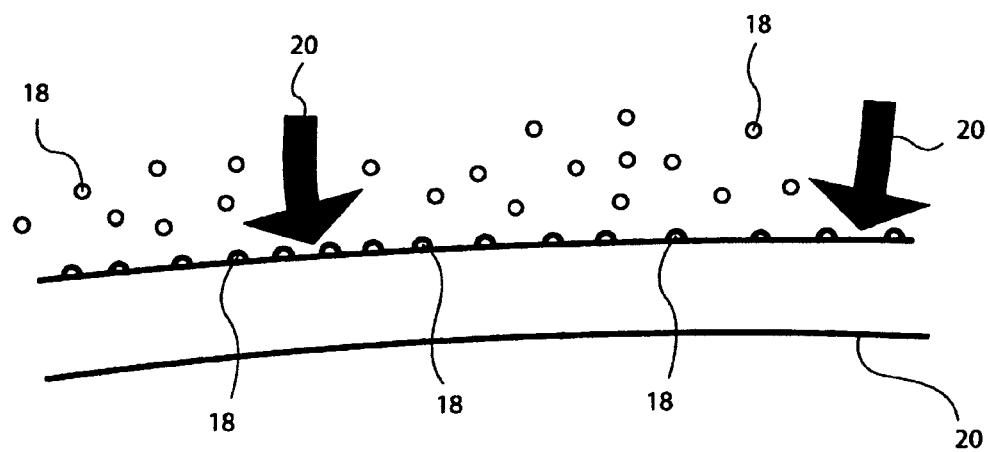
FIG. 6 shows a close-up view of the compressible applicator's surface indentations against the restorative layer.

FIGS. 4A to 4C show the sequential mechanics of resin compression. FIG. 5 shows adaptive compression along a contoured surface. FIG. 6 shows the interaction of an applicators indented surface with a resin layer.

The compressible composite resin shaping instrument of present consists of an elongated cylindrical gripping handle 2 with having recessed holes, or docking apertures 4 at its terminations. The handle 2 also has a number of circumferential gripping grooves 6 desirably inset from its terminations that 6 permit a stable grip during operation. The docking apertures 4 are cylindrical bores with a depth and diameter that is desirably sized to accept and interlock with an elongated extension or compressible insert 8. It is ideally made from a reusable, auto-clavable metal or disposable plastic. The compressible insert 8 is comprised of two fundamental portions. The first portion is the rigid cylindrical extension or insert body 10. The second portion is a pliant volume, soft mass or compressible applicator 14. The compressible applicator is bonded to the insert body and is designed for operative interaction.

The insert body 10 has two functional terminations. The first termination is designated by a gently curved, tapered portion that ends in an abruptly flared disc, platform, or applicator holder 12. The holder 12 has a flat circular face to produce a stable bonding surface for the compressible applicator 14 (FIG. 3A). The holder's size and thickness can be variably altered to suit a variety of compressible applicator 14 sizes (Size determined by operative demands). The insert body's 10 second termination is designated by a very subtle reversal in taper generally near the insert body's 10 mid point. This reversal in taper or insert taper point 16 signals a very subtle diameter reduction that culminates with a rounded hemispherical end. The gradual tapering designated by the insert taper 16 is designed to create a mechanically determined stopping point when inserted into the handles 2 apertures 4 (FIG. 2). Thus, this stopping point creates a frictional interlocking for operational stability. The degree of frictional interlocking interlock is determined by the degree of force by which the insert body 10 is placed into the handles 2 apertures 4.

The compressible applicator 14 is a generally cylindrical volume made from a soft pliant foamed material or suitably pliant rubberized material such as silicone. It is desirably compressible to simultaneously permit non-impressive restorative material adaptation (will not produce instrument markings) while retaining enough density to permit adequate restorative shaping and sculpting capabilities. The compressible applicators 14 surface additionally contains a plurality of desirably sized pockets, depressions or surface indentations 18 (FIGS. 3A and 3B). The primary function of the indentations is to desirably reduce the operative contact area of the compressible applicator with a restorative material. Desirably sized Indentations 18 can be created by using an appropriate foamed material or by a molding process. Note: the combination of the applicator's 14 compressibility and surface indentations 18 produces a unique ability to interact and sculpt restorative materials with minimal impression and minimal adherence.

FIGS. 4A to 4C illustrate this combination with a sequential compression of an applicator 14 against a restorative material 20. First, with applied pressure, the applicator 14 is designed to compressively adapt to both the restorative material and an underlying surface. As it compresses, it creates compressible forces 22 that generate a circumferential expansive movement 24 of the restorative material 20 (FIG. 4B). Because the applicator adaptively conforms (FIG. 5) it does not leave marks or indentations, and the restorative material is non-impressed after compression and expansion (FIG. 4C). Secondly, because the surface indentations 18 reduce the surface contact between the applicators and the restorative material 20 (FIGS. 5 to 6), there is minimal sticking or adherence. This dynamic serves to reduce the event of pulling the material away from a tooth surface upon withdrawal 28.

The compressible composite shaping instrument can be made from any number of materials and fabrication processes. For example, the handle 2 may be fabricated from any number of metals or alloys. Fabrication may be accomplished by casting, rolling, extruding, lathing, CNC machining, or any other suitable process. Additionally, the handle 2 can be made from any number of plastics, ceramics, or other synthetic materials that can be injection molded, milled, or lathed into configuration. The compressible insert 8 may be made from any number of materials. For example, the insert body 10 can be made from metals, alloys or disposable plastics such as acrylic. Any synthetic material that is appropriate and non-toxic may be utilized. Forming the insert body 10 may be achieved via milling, lathing, extruding, or injection molding. The compressible applicator 14 can be made from any number of foamed materials that are sufficiently pliant and compressible, and are suitably wear resistant. The indentations 18 may also be formed by a foaming process or by molding process. The size of the indentations 18 is highly variable and dependent upon optimal clinical function. If a foamed material is used, it may be open or closed cell. Additionally, the applicator 14 can be made from a suitably compressible silicone, rubber or other synthetic.

FIGS. 7-10 ADDITIONAL EMBODIMENTS

Figure 7:
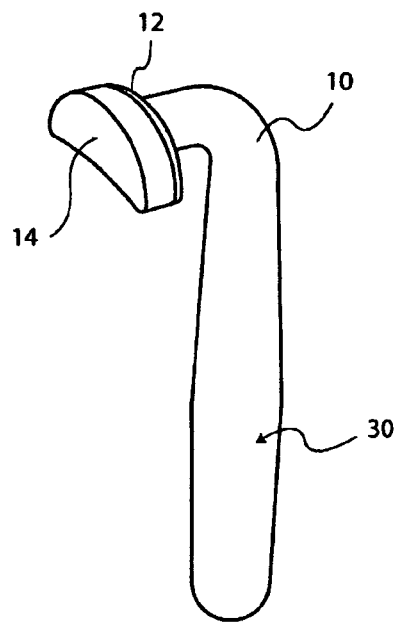
FIG. 7 shows a gum-line compressible insert embodiment having a compressible crescent shaped gingival applicator.
Figure 8:
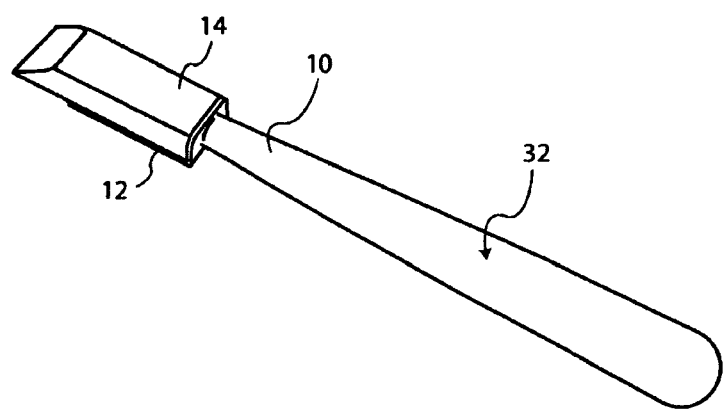
FIG. 8 shows an inter-proximal compressible insert embodiment having a thin tapered wedge-shaped applicator.

There are a number of configuration changes that facilitate a full range of restorative applications. These configurations are intended to address the anatomic demands of dental anatomy. For example, FIG. 7 shows a gum line compressible insert 30. This insert has a more aggressively angled applicator holder 12 and a crescent shaped compressible applicator. The crescent shape is desirably contoured to provide optimal adaptation for gingival regions. FIG. 8 shows an inter-proximal compressible insert 32. It has a straight insert body 10 with box-like applicator holder 12 that holds a thin, wedge-shaped compressible applicator 14. This thin wedge shape is designed to compressively adapt a restorative material 20 into inter-proximal tooth spaces.

Figure 9:
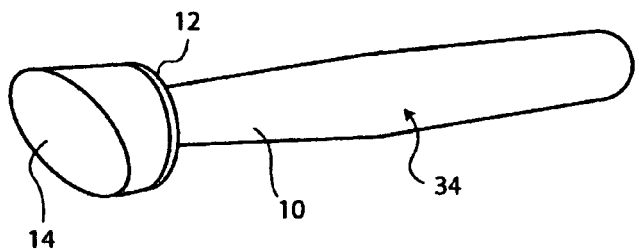
FIG. 9 shows a wedge brush compressible insert embodiment having an acutely angled applicator.
Figure 10:
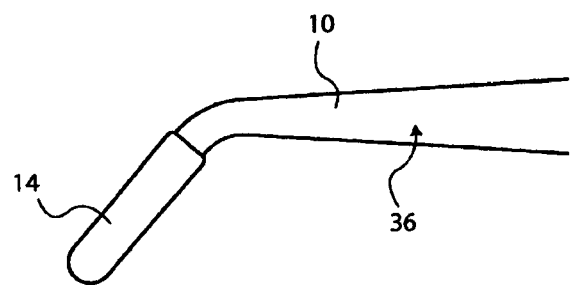
FIG. 10 shows a condensing compressible insert embodiment having an elongated cylindrical condensing applicator.

FIG. 9 shows a wedge brush compressible insert 34. This insert has a straight body 10 with a cylindrical compressible applicator 14 that has an acutely wedged face. This face is designed for detailing and brushing applications where smoothing or gentle adaptation is required. FIG. 10 shows a condensing compressible insert 36. The condensing insert 36 has an elongated cylindrical compressible applicator with a rounded hemispherical end. This insert has no apparent applicator holder. The compressible applicator 14 in this case is molded to or bonded to the insert body 10.

FIGS. 19-41 ALTERNATIVE EMBODIMENTS

There are various possibilities with regard to compressible composite resin shaping instrument. Compressible inserts 8 are highly variable and may include a great variety of features and configurations intended to enhance operative performance and ease of use. All are highly variable and may have alternative shapes, coatings, and multiple terminations.

Figure 19:
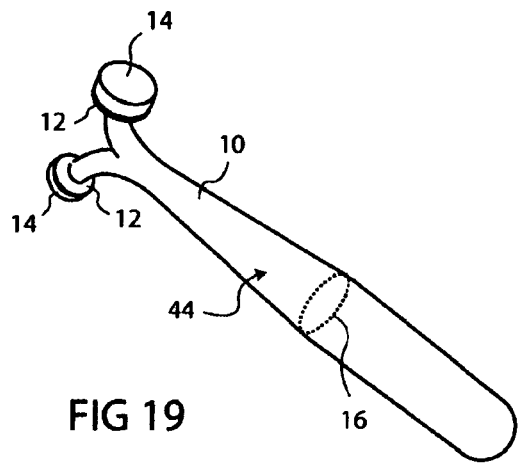
FIG. 19 shows a multi-headed compressible insert having two compressible applicators.
Figure 20:
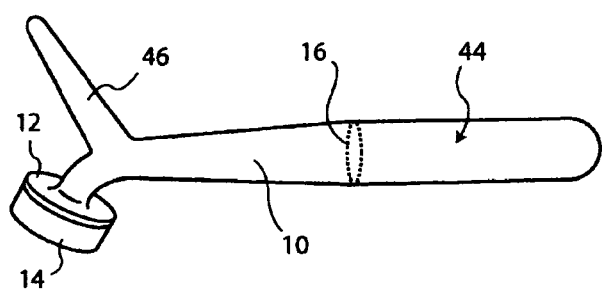
FIG. 20 shows a multi headed compressible insert having a single compressible applicator and shaping blade.
Figure 21A:
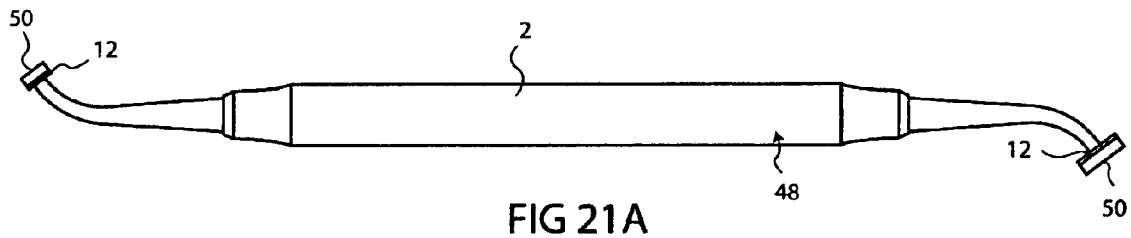
FIGS. 21A to 21E show various aspects of an integrated compressible instrument having permanently attached inserts and independently applied adhesive compressible applicators.
Figure 21B:
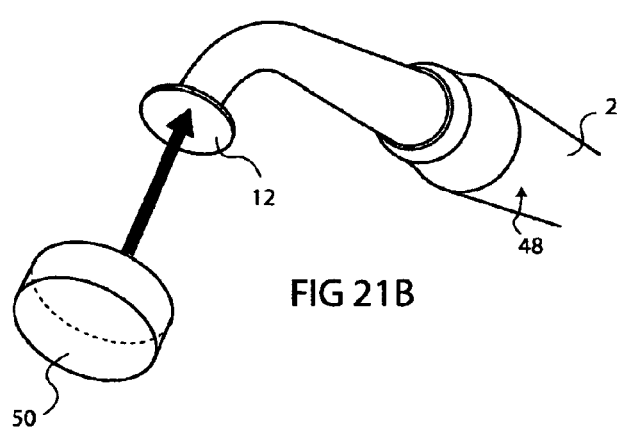
Figure 21C:
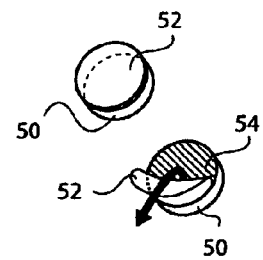
Figure 21D:
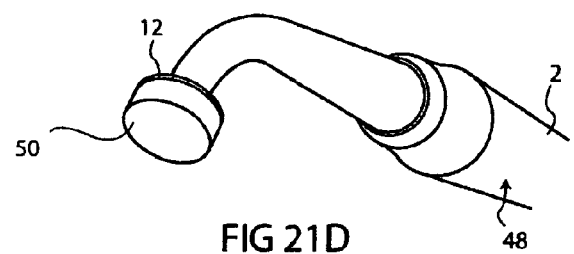
Figure 21E:
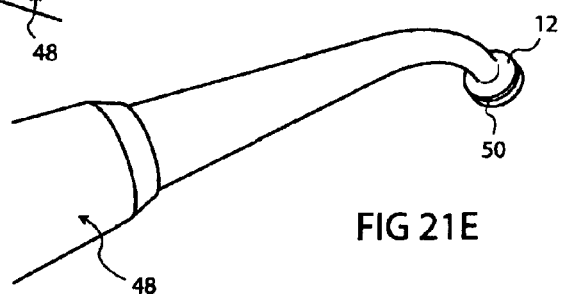

For example, FIG. 19 shows a multi-headed compressible insert 44. This is designed to increase workflow by allowing the operator 38 rapid access to multiple applicator sizes and shapes. FIG. 20 shows a multi-headed insert 44 having a compressible applicator 14 and a shaping blade 46. This configuration is designed to permit rigid shaping via the blade 46 along with compressible adaptation from the compressible applicator 14.

FIGS. 21A to 21E show views of a compressible composite resin shaping instrument 48 that has permanently fused inserts (similar to conventional instrumentation). This embodiment utilizes independently applied self adhesive compressible applicators 50. The adhesive applicator 50 has a peel away layer 52 that exposes and adhesive surface 54. This allows an operator to adhesively affix the applicator 50 to the instruments 48 applicator holders 12.

Figure 22A:
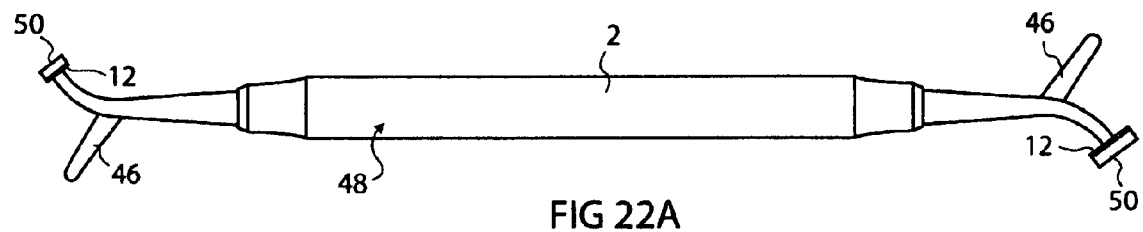
FIGS. 22A to 22C show various aspects of an integrated compressible instrument having permanently attached inserts, compressible applicators and shaping blades.
Figure 22B:
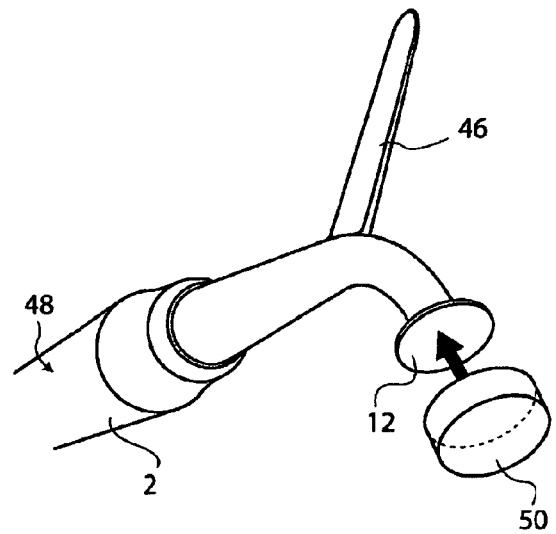
Figure 22C:
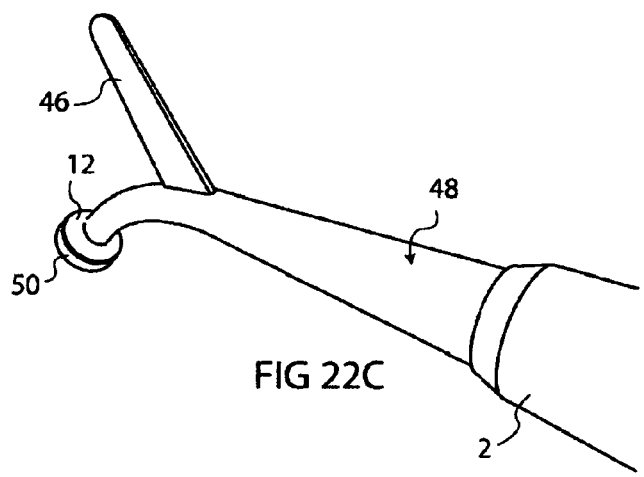

FIGS. 22A to 22C show various views of a compressible tool 48 that has permanently fused inserts, two compressible applicators 14 and two shaping blades 46. This embodiment utilizes self adhesive compressible applicators 50.

Figure 23:
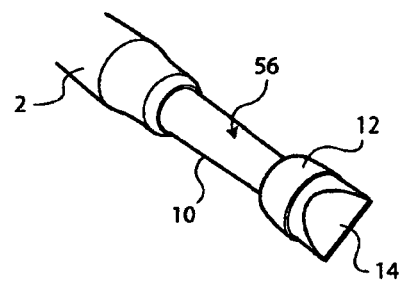
FIG. 23 shows views of a chisel shaped compressible insert.
Figure 24:
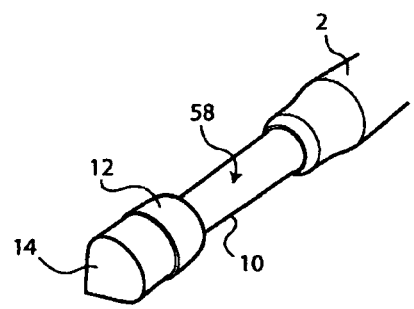
FIG. 24 shows views of a conical shaped compressible insert.
Figure 25:
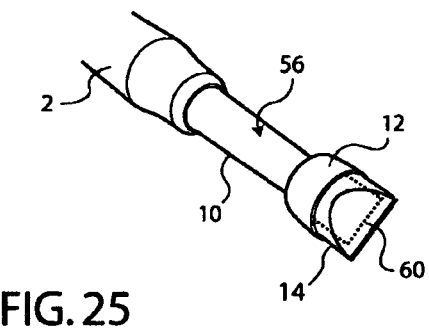
FIG. 25 shows views a compressible insert with an internally integrated applicator stabilizer.

FIG. 23 shows a chisel shaped compressible insert 56. FIG. 24 shows a conical compressible insert 58. FIG. 25 shows a compressible insert 8 with an internal tip stabilizer 60. The stabilizer 60 is a rigid plastic that provides internal operational stability.

Figure 26:
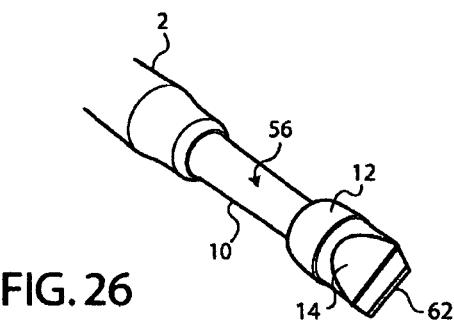
FIG. 26 shows views a compressible insert having an externally integrated applicator stabilizer.

FIG. 25 shows an insert 8 with an internal tip stabilizer 62. The stabilizer 62 is a more rigid material designed to support greater compressive forces 22. FIG. 26 shows an insert 8 with an external tip stabilizer 62.

Figure 27:
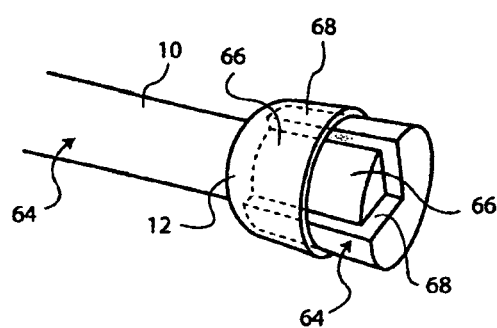
FIG. 27 shows views of a multi core compressible insert.

FIG. 27 shows a compressible insert 8 with a multi-core compressible tip 64. The multi-core tip 64 has an external layer 66 that encased a sheathed core 68. The materials are composed varying densities and compressibility.

Figure 28:
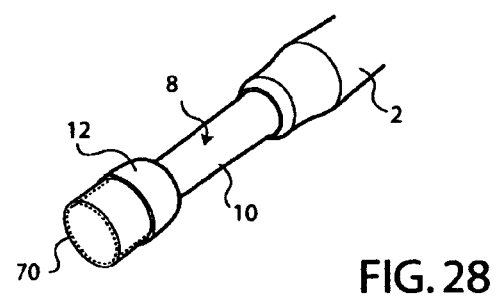
FIG. 28 shows a compressible applicator having a non-stick encasement.

FIG. 28 shows a compressible insert 8 that has a coated compressible applicator 70. The coating can be any material that sufficiently aids performance and nonstick properties.

Figure 29:
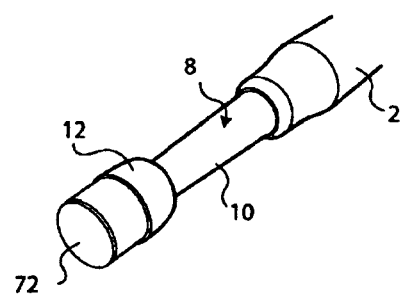
FIG. 29 shows a compressible applicator having a non-stick veneer bonded to its operative surface.

FIG. 29 shows a compressible insert 8 that has a veneered applicator 72. The veneering is applied to the operative surface of the applicator.

Figure 30A:
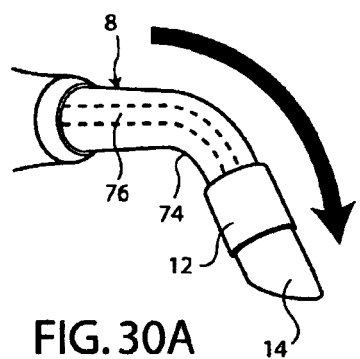
FIGS. 30A to 30B show various views of a compressible applicator having a flexible body and flexion core insert being bent along X, Y and Z axes.
Figure 30B:
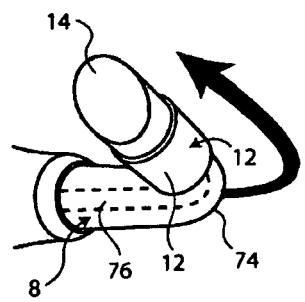

FIGS. 30A and 30B show a compressible insert 8 with a flexible body 74. The flexible body 74 has an internally located flexion core 76 that permits X, Y, Z axis space flexibility. The core can be made from a flexible steel or other suitable metal.

Figure 31:
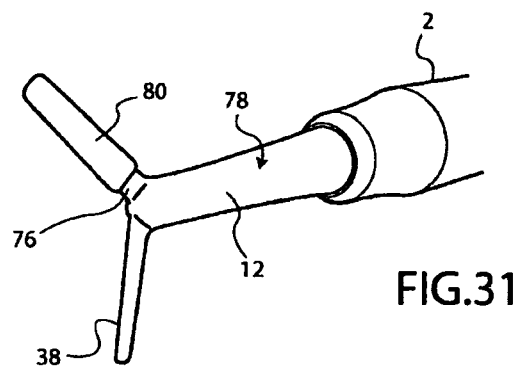
FIG. 31 shows a compressible insert having a shaping blade with a compressible sheath.

FIG. 31 shows a multi headed compressible insert 80 with a compressible sheathed shaping blade 78.

Figure 32A:
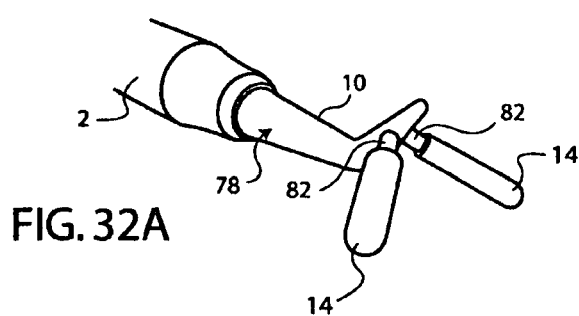
FIGS. 32A-32C show a multi-tipped insert with snap-in compressible applicators.
Figure 32B:
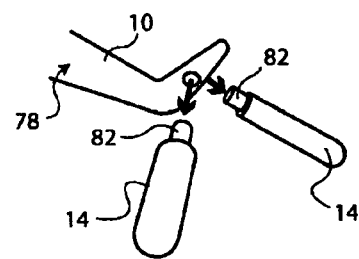
Figure 32C:
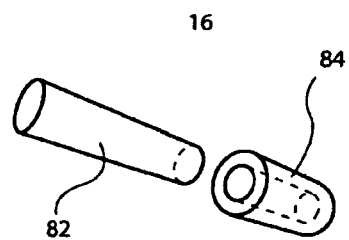

FIGS. 32A and 32C show a multi tipped compressible insert 80 that utilizes snap in compressible applicators 82. The snap in applicators have a bonded compressible sheath 84.

Figure 33:
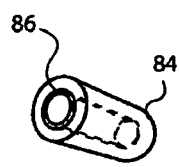
FIG. 33 shows a compressible sleeve with a reinforcing sleeve liner.

FIG. 33 shows a compressible sheath 84 with a stabilizing plastic sheath liner 86. The liner 82 is semi rigid and facilitates operational stability.

Figure 34A:
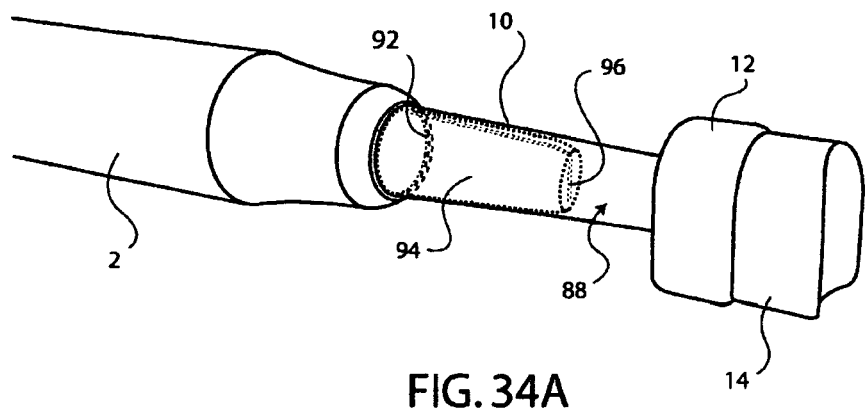
FIGS. 34A to 34B show a compressible insert having a docking aperture and a snapping ring with a handle having a docking extrusion and a snapping groove.
Figure 34B:
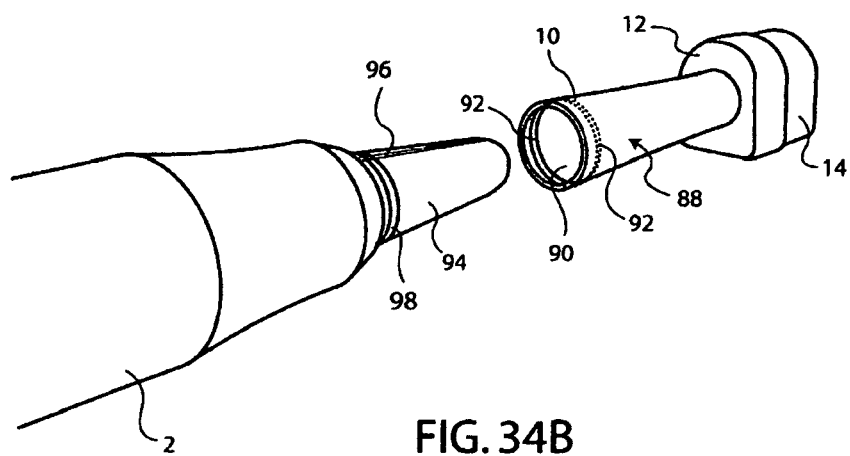

FIGS. 34A and 34B shows an aperture compressible insert 88 that has a docking aperture 90 and snapping ring 92. This permits an interlocking engagement with a handle's 2 docking extrusion 94. The handle docking extrusion 94 has a friction groove 96 and a circumferential snapping groove that correlates with the aperture compressible inserts 88 snapping ring.

Figure 35A:
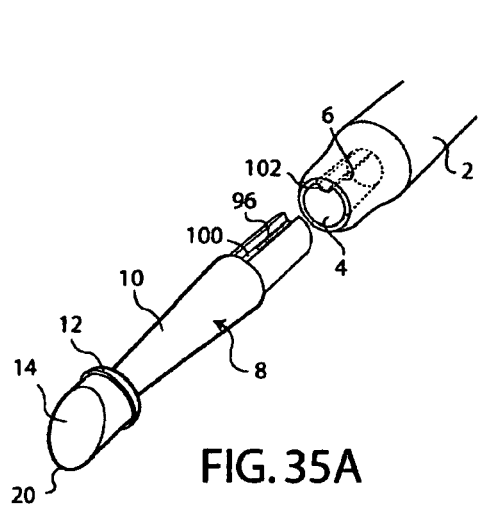
FIGS. 35A to 35D show various views of a compressible insert with an anti-rotational channel, friction groove, and a handle having an anti-rotational extrusion.
Figure 35B:
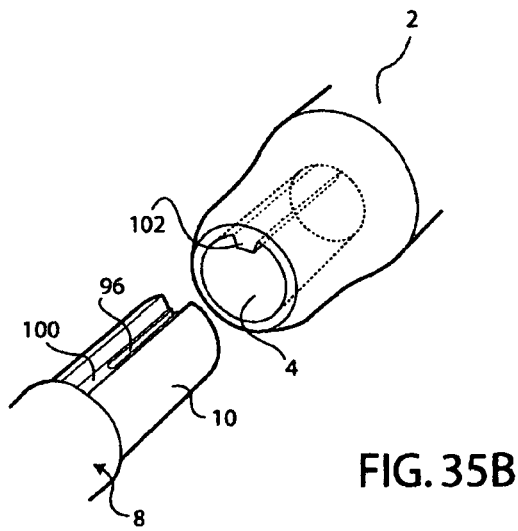
Figure 35C:
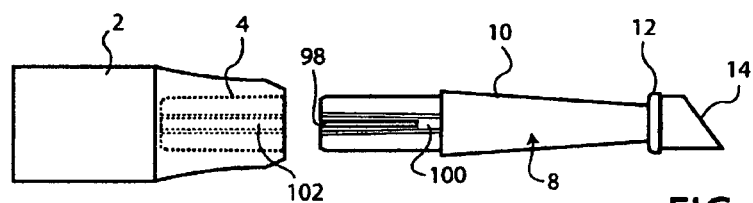
Figure 35D:
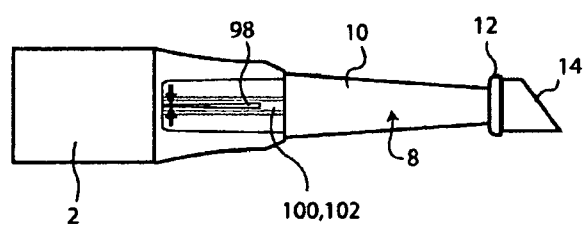

FIGS. 35A to 35B show various views if a compressible insert 8 having a friction groove 96 and an anti rotational groove 100 that correlates with a handles 2 anti-rotational extrusion 102.

Figure 36:
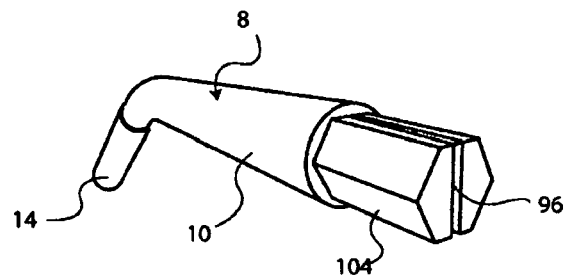
FIG. 36 shows a compressible insert with a hexagonal insert body.

FIG. 36 shows an insert 8 with a friction groove 96 and a faceted insert body 104.

Figure 37:
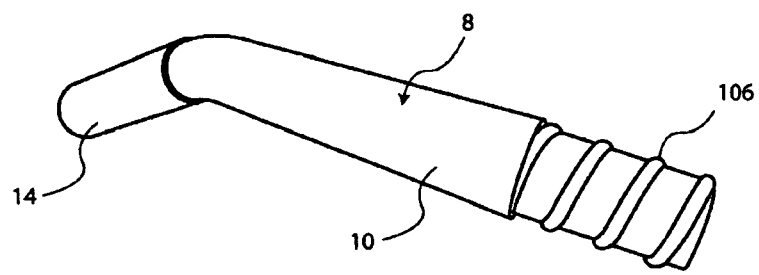
FIG. 37 shows a compressible insert with a threaded insert body.
Figure 38:
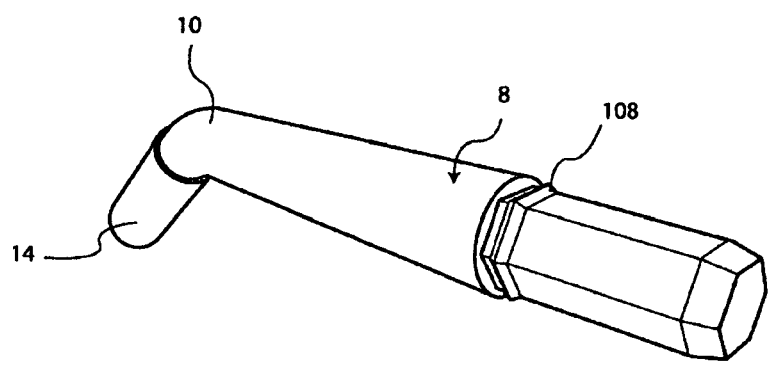
FIG. 38 shows a compressible insert with a snap insert body.
Figure 39A:
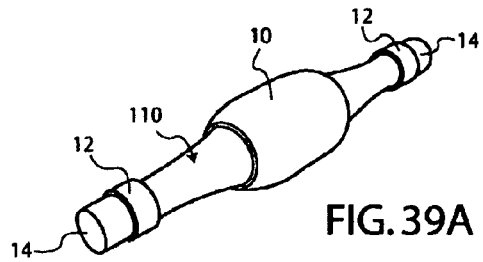
FIGS. 39A to 39B show views of a grasp-able compressible insert.
Figure 39B:
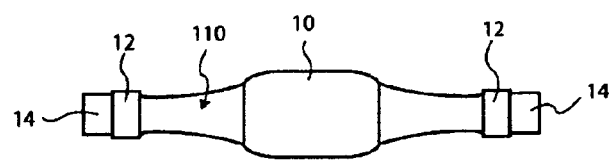
Figure 40:
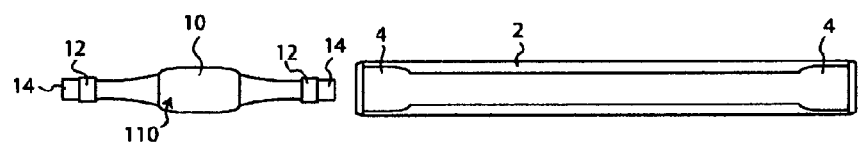
FIG. 40 shows a grasp-able compressible insert docked with a handle.
Figure 41:
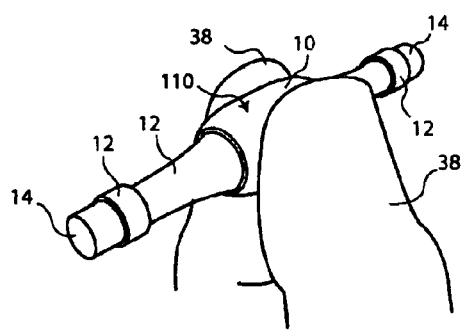
FIG. 41 shows an operator gripping a grasp-able compressible insert.

FIG. 37 shows an insert 8 with a threaded insert body 106.

FIG. 29 shows an insert 8 with a snap insert body 108.

FIGS. 39A to 41 show a grasp-able compressible insert that can either be docked with a handle 2 or grasped by an operator 38.

FIGS. 11A-18C, 42A-42C OPERATIONS

Figure 11A:
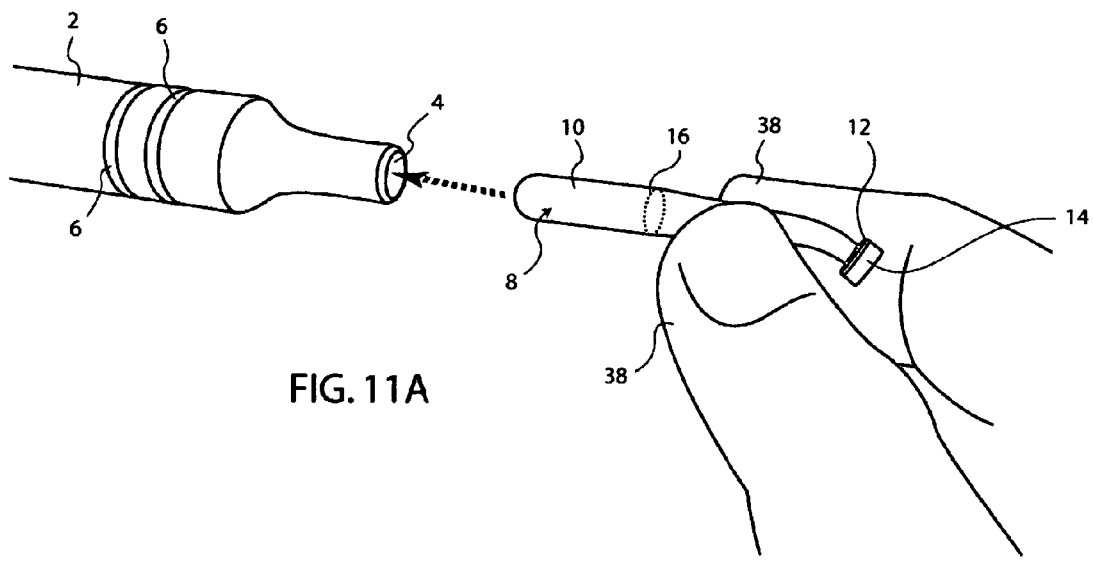
FIGS. 11A to 11B show an operator inserting a compressible insert into a gripping handle's insertion aperture.
Figure 11B:
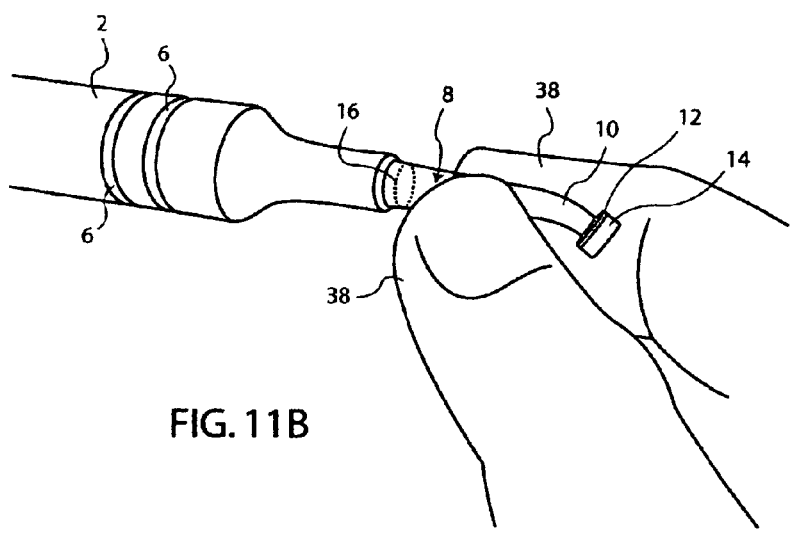
Figure 12A:
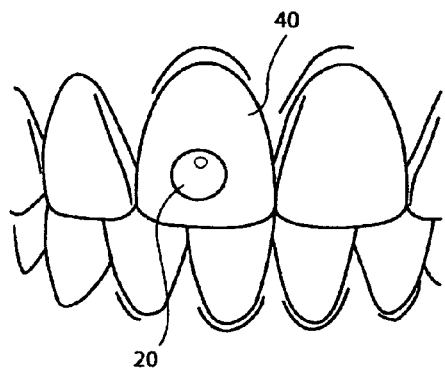
FIGS. 12A to 12C show a progressive sequence of a compressible applicator applying a restorative material to an anterior tooth surface.
Figure 12B:
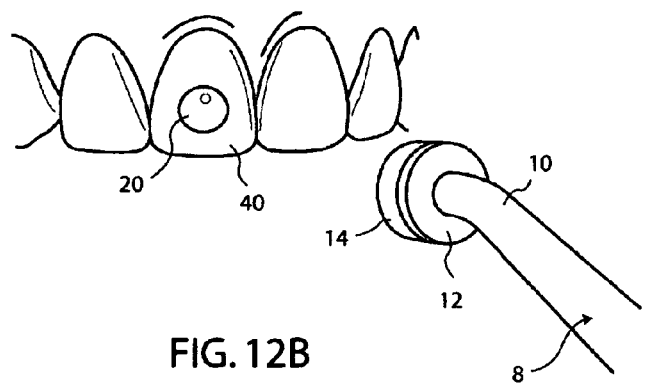
Figure 12C:
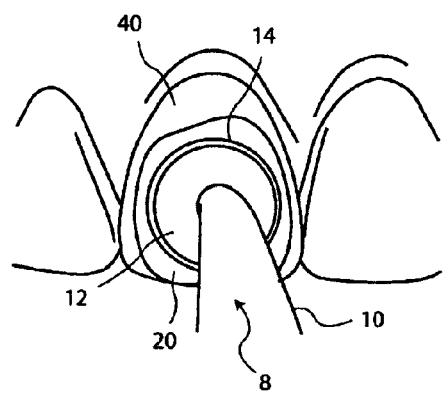
Figure 13:
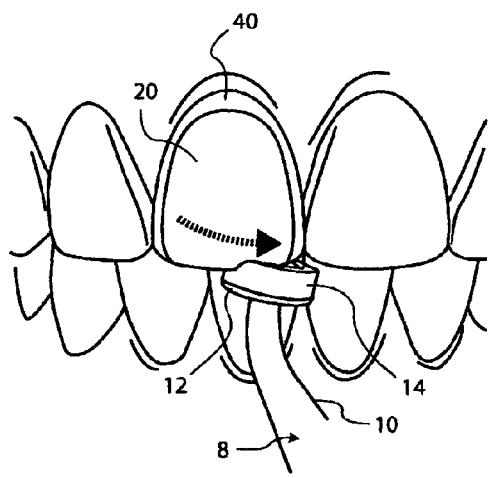
FIG. 13 shows the incisal edge of a tooth being brushed to remove excess resin.
Figure 14A:
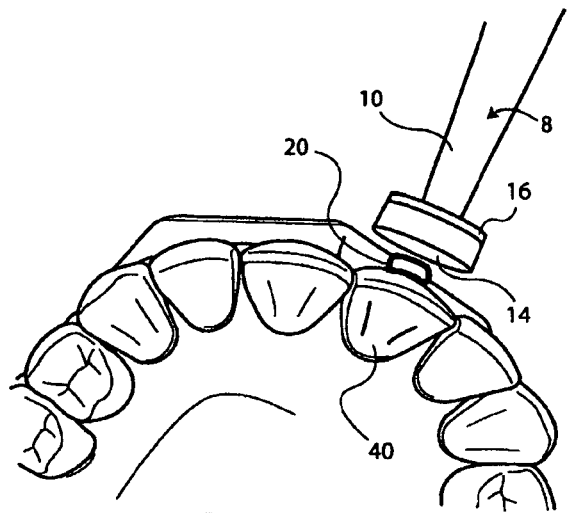
FIGS. 14A to 14D show an inferior view of a compressible applicator sequentially applying a restorative material to an anterior tooth surface.
Figure 14B:
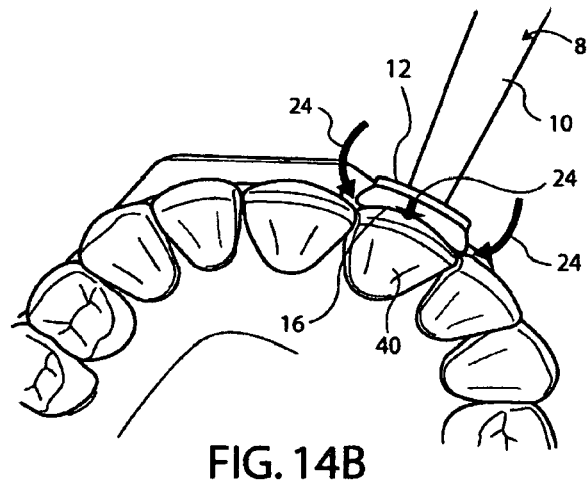
Figure 14C:
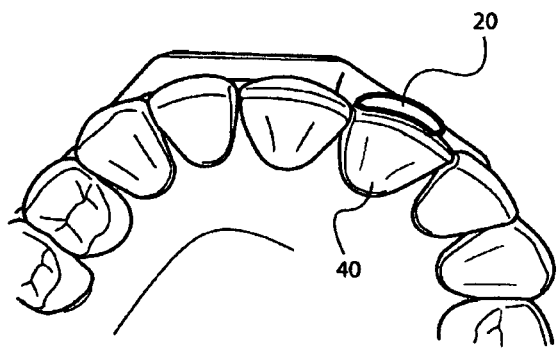
Figure 14D:
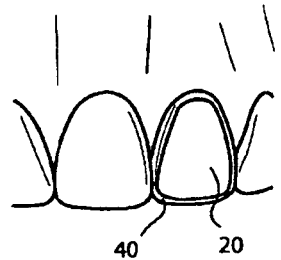

The manner of using the compressible restorative instrument is dependent upon procedural requirements. For an anterior tooth 40, an operator selects a compressible insert 8 and snugly places the insert body 10 into one of the handles the apertures 4 (FIGS. 11A and 11B). After the insert 8 is snugly in place, a desired amount of restorative material 20 is placed onto the anterior tooth 40 surface (FIG. 12A). Next, the compressible applicator 14 is guided toward the prepared anterior tooth 40 (FIGS. 12B and 14A) and compressed repeatedly against the adhered restorative material 20 (FIGS. 12C and 14B). This is repeated along with brushing motions until the anterior tooth surface 40 is desirably layered. (FIGS. 14C and 14D). In the event of excess restorative material 20 extending beyond the tooth's 40 incisal edge, the operator 38 can brush the edge to remove excess restorative material (FIG. 13).

Figure 15:
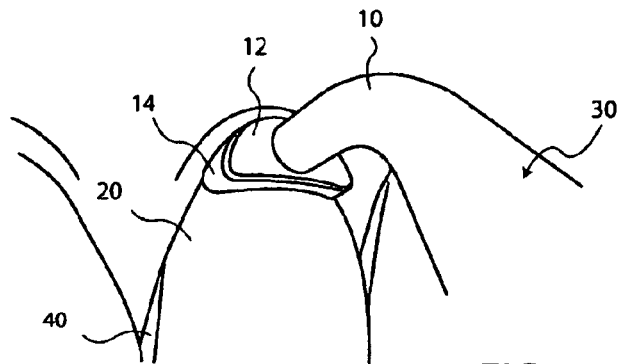
FIG. 15 shows a gum-line compressible insert adapting composite resin to an anterior tooth's gingival region.
Figure 16A:
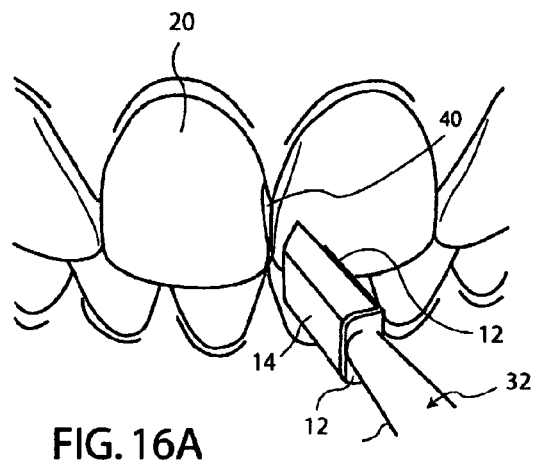
FIGS. 16A to 16B show an inter-proximal compressible insert adapting composite resin to an anterior tooth's inter-proximal space.
Figure 16B:
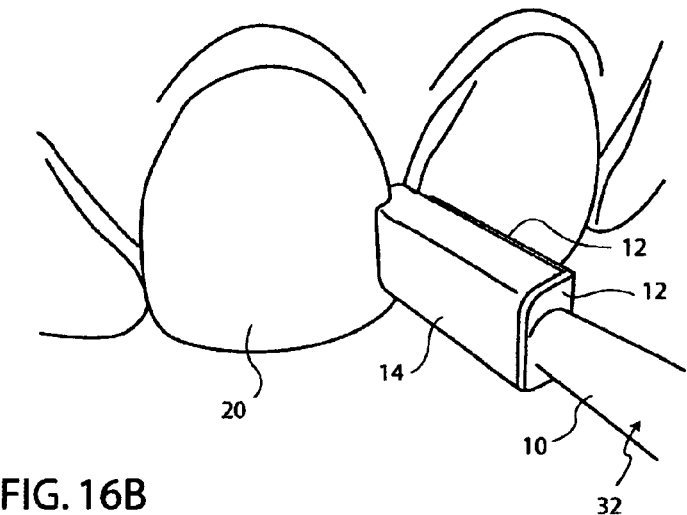
Figure 17A:
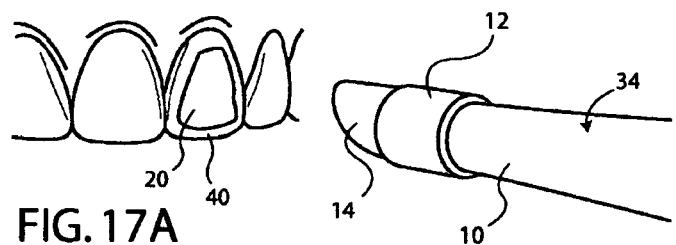
FIGS. 17A to 17D show various views of a compressible wedge brush insert smoothing a restorative material by directionally brushing it.
Figure 17B:
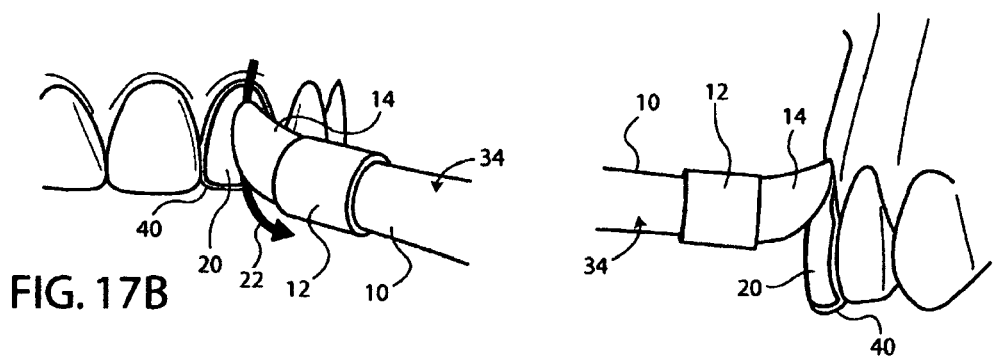
Figure 17C:
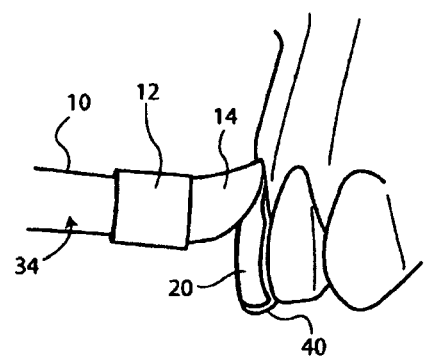
Figure 17D:
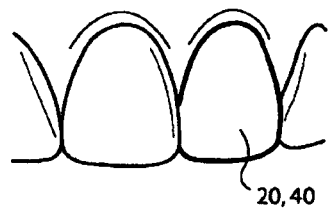

Next, the operator can insert a gum-line compressible insert 30 into the handle's 2 other aperture 4 (not shown) to adapt the restorative material gingivally (FIG. 15). The contoured crescent applicator 14 is compressed into the gum line. When this is determined to be satisfactory, an operator 38 can replace one of the previous inserts (not shown) and insert an inter-proximal compressible insert 32. The inter-proximal compressible insert 32 is guided into the anterior tooth's 40 inter-proximal space (FIG. 16A) to compressively adapt the restorative material around the tooth's 40 edge (FIG. 16B). After sufficient inter-proximal adaptation, the operator 38 can optionally use a wedge brush compressible insert 34. The wedge brush 34 is gently brushed against the anterior tooth 40 to both pull and smooth the restorative material 20 prior to curing (FIGS. 17A to 17D). This process is repeated until the restoration is complete.

Figure 18A:
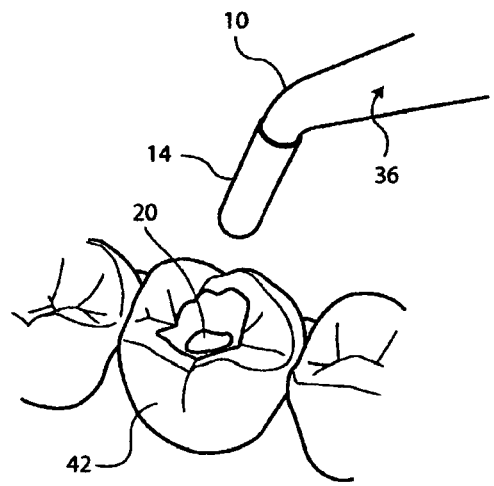
FIGS. 18A to 18C show various views of a condensing compressible insert compressively adapting resin into a prepared posterior tooth.
Figure 18B:
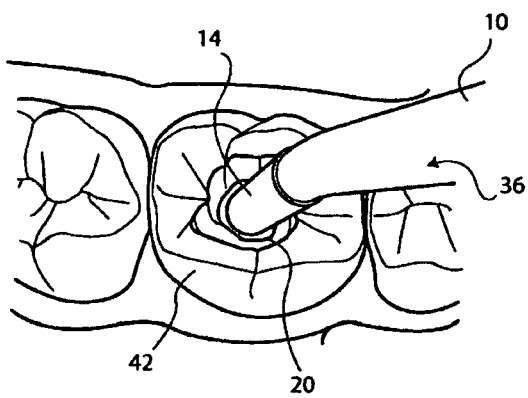
Figure 18C:
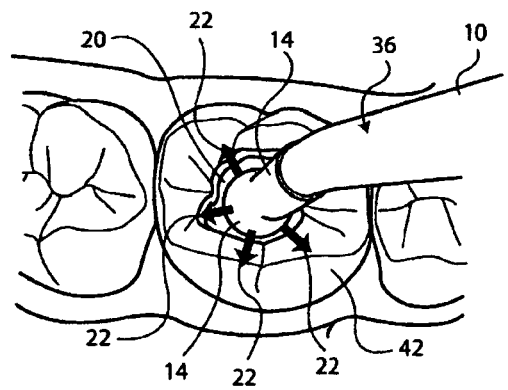

For a posterior restoration, an operator 38 first places a desired amount of restorative material 20 into a prepared posterior tooth 42. Next a condensing compressible insert 36 is placed into a handle's 2 aperture 4. The operator proceeds to compressively condense and adapt the material 20 in a conventional fashion (FIGS. 18A to 18C), curing restorative increments as needed.

Figure 42A:
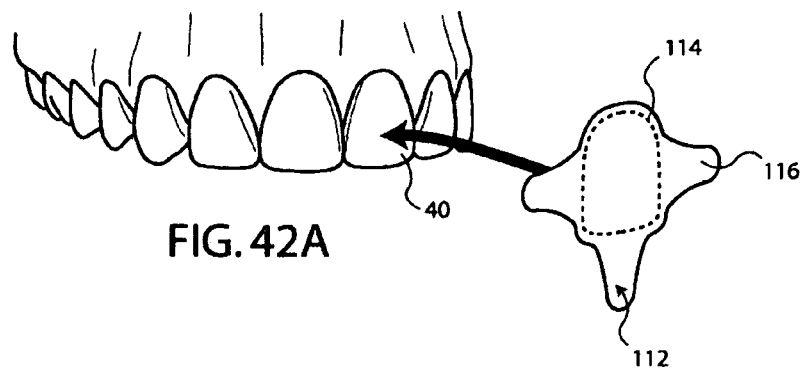
FIGS. 42A to 42C show a compressible insert applying a pre-formed veneer to an anterior tooth surface.
Figure 42B:
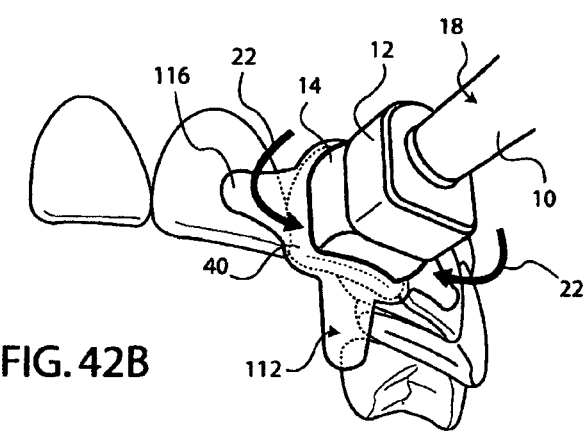
Figure 42C:
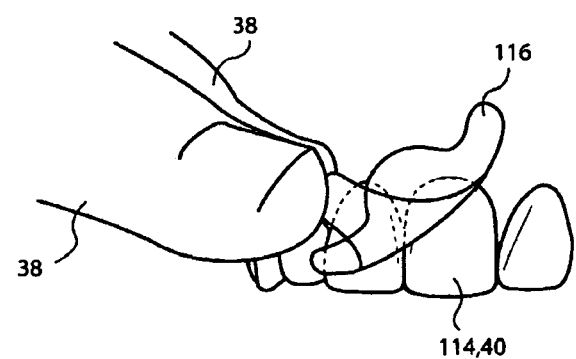

FIGS. 42A to 42C shows an alternative use and operation for the compressible dental restorative shaping instrument. It involves the application of a preformed veneer 112 having a uniformly thick preformed uncured restorative layer 114 with an attached applicator sheath 116. First, the veneer 114 is applied to an anterior tooth 40 so that the resin layer 114 adheres to the tooth and applicator sheath 116 faces outward (FIG. 42A). Next, a compressible insert's 8 applicator is compressed and massaged against the applicator sheath's 116 exterior to adapt the restorative layer to an anterior tooth's 40 surface (FIG. 37B). During adaptation, the soft compressible applicator 14 permits an adaptive compression that is non-impressive and permits a non impressed smooth transfer of the resin layer from the applicator sheath 116 to the anterior tooth's 40 surface. The applicator sheath 116 is then removed after desirable adaptation (FIG. 37C).

ADVANTAGES

From the description above, a number of advantages of the Compressible Composite Shaping Instrument become evident:

a) The hybrid nature of the foam applicators permit the instrument to serve as both a shaping instrument and or a brush, economizing the operative workflow.
b) The docking nature of the insert and handle will permit a wide variety of customized choices by an operator.
c) The compressible tip dynamics will allow for a tactile and reactive adjustability that is not attainable with rigid instrumentation.
d) The enveloping compressive adaptation of resin will allow for a minimally impressive adaptation of restorative materials that will drastically reduce finishing time.
e) Color coding compressible inserts will lessen chair side confusion with instruments.
f) The universal docking mechanism can allow for a multitude of tip varieties.

CONCLUSION, RAMIFICATIONS AND SCOPE

Accordingly, the compressible restorative dental shaping instrument superiorly adapts restorative materials to teeth. Foam's compressible, non-sticky surface allows resin to be compressively adapted, brushed, and feathered seamlessly into tooth anatomy. Additionally, the compressive dynamic allows the resin to be adapted to thinness not achievable with standard rigid instruments. The porous nature of foam also substantially minimizes adherence to restorative materials and helps to absorb highly liquid restorative materials. Furthermore, the compressible composite resin instrument has the additional advantages in that:
  It permits rapidly changeable tip assortments for any anatomical requirement
  It eases multiple layering of resins by allowing seamless adaptation of resin into previously photo-cured layers
  Provides comfort to the patient by limiting the use of potentially injurious metal instruments
  Simplifies the process with disposability
  Simplifies direct veneer restorative process by allowing resin to be compressively applied through an emulsion
  Minimizes resin pullback
  Can absorb over application of low viscosity restorative materials
  Foam drastically reduces adherence to resin Although the description above contains much specificity, these should not be construed as limiting the scope of an invention but as merely providing illustrations of the presently preferred embodiments for this invention. For example, the handle may assume any shape including symmetrical and asymmetrical shapes. The handle may have any number of docking terminations or docking extrusions to accept compressible inserts. The handle may be made of any suitable material for optimal operation.

The compressible inserts may have any shape, length, thickness, and any number of necessary terminations as dictated by optimal operative use. It may be made from any suitable metal or plastic material. The insert may optionally contain internal application chambers for holding desired restoratives or other medicaments that may absorb into the foam tip and deliver upon compression.

The insert may have any number of grooves, friction channels, threading or other snapping devices to allow secure docking with a handle. All of the above features may be incorporated in any configuration or may be eliminated all together if need arises. For example, magnets or other attachable means may be incorporated to attach the insert to a handle. Additionally, adhesives may be applied to any and all applicable surfaces where deemed necessary.

The compressible applicator may assume any shape, have any density with any number of specialized terminations. The indentations can be of any number and any size deemed necessary. In the event of restorative demand, the indentations can be removed altogether. The tips may have any number of specialized coatings, encasings, or emulsions to optimize compression, adaptation and non-stickiness while interacting with restorative materials. For example, the tip may be treated with Teflon or other non-stick agents. Adhesives may be applied to any and all applicable surfaces where deemed necessary. The tip may have partial or full encasing of a soft rubberized or silicone material. Furthermore, tips can be multi-layered or multi-cored. The cores can be of any number and be comprised of differential materials. For example, a foam core exterior may have a rubberized interior core. Additionally, the tip can be made of any material that is suitably compressible. Lastly, the compressible restorative dental shaping instrument can be made as an all in one material instrument that can embody and incorporate all of the above attributes in any number and or combination.

What is claimed is:

1. A method of dental restoration comprising:
providing a gripping body having a docking portion;
attaching a compressible shaping member to the docking portion;
applying a dental composite material to a tooth, the dental composite material being sculptable; and
displacing the dental composite material on the tooth with the compressible shaping member;
wherein the compressible shaping member is compressed by the displacement;
wherein the compressible shaping member is made of a closed-cell material and includes a plurality of indentations configured to reduce surface area contact with the dental composite material during the displacement;
wherein the compressible shaping member includes a rigid docking portion and a compressible portion, the compressible portion being configured to contact the dental composite material during the displacement;
wherein the rigid docking portion of the compressible shaping member is configured to removably dock with the docking portion of the gripping body.

2. The method of claim 1, further comprising repeatedly displacing the dental composite material to sculpt the dental composite material.

3. The method of claim 1, wherein the compressible shaping member includes a silicone material.

4. The method of claim 1, wherein the compressible shaping member adaptively conforms to a surface of the dental composite material during the shaping.

5. The method of claim 1, wherein the shaping generates circumferential expansive movement of the dental composite material.

6. The method of claim 5, wherein the dental composite material is substantially non-impressed by the compressible shaping member after the circumferential expansive movement.

7. The method of claim 1, wherein the compressible shaping member is made of a foamed material.

8. The method of claim 1, wherein the compressible shaping member is made of a rubberized material.

9. The method of claim 1, further comprising detaching the compressible shaping member from the dental instrument; and
attaching a second compressible shaping member to the dental instrument.

10. The method of claim 9, wherein the second compressible shaping member is shaped differently than the compressible shaping member.

11. The method of claim 10, wherein the second compressible shaping member is an inter-proximal compressible insert configured to compressively adapt the restorative material around an edge of the tooth.

12. A method of dental restoration comprising:
applying a dental composite material to a tooth;
attaching a removable insert to a dental instrument, the removable insert having a compressible shaping member, the compressible shaping member configured to reduce surface area contact, and leave minimal imprint, with the dental composite material; and
micro-manipulating the dental composite material on the tooth with the compressible shaping member;
wherein the compressible shaping member is compressed by the micro-manipulation;
wherein the dental composite material is light-curable and sculptable;
wherein the compressible shaping member is made of a closed-cell material and includes a plurality of surface indentations configured to reduce adherence between the dental composite and the compressible shaping member;
wherein the compressible shaping member includes a rigid docking portion and a compressible portion, the compressible portion being configured to contact the dental composite material during the displacement;
wherein the rigid docking portion of the compressible shaping member is configured to removably dock with the docking portion of the gripping body.

* * * * *